United States Patent [19]

Maeda et al.

[11] Patent Number: 4,725,722
[45] Date of Patent: Feb. 16, 1988

[54] AUTOMATIC FOCUSING METHOD AND APPARATUS UTILIZING CONTRASTS OF PROJECTED PATTERN

[75] Inventors: Shunji Maeda, Yokohama; Hiroshi Makihira, Fujisawa; Hitoshi Kubota, Yokohama, all of Japan

[73] Assignee: Hitachi, Ltd., Tokyo, Japan

[21] Appl. No.: 850,682

[22] Filed: Apr. 11, 1986

[30] Foreign Application Priority Data

Apr. 12, 1985 [JP] Japan .................................. 60-76575

[51] Int. Cl.⁴ .............................. G01J 1/20; G01J 1/36
[52] U.S. Cl. ......................................... 250/201; 250/204; 356/4
[58] Field of Search ................... 250/201 AF, 201 PF, 250/204, 201 DF; 356/4; 354/403; 369/44, 45, 46

[56] References Cited

U.S. PATENT DOCUMENTS

| | | | |
|---|---|---|---|
| 3,706,492 | 12/1972 | Roblin et al. | 250/201 AF |
| 3,719,421 | 3/1973 | Poilleux et al. | 356/4 |
| 3,912,922 | 10/1975 | Lacotte et al. | 250/201 AF |
| 3,925,603 | 12/1975 | Naruse et al. | 250/201 DF |
| 3,970,842 | 7/1976 | Nanba | 356/4 |
| 4,123,652 | 10/1978 | Bouwhuis | 250/204 |
| 4,577,095 | 3/1986 | Watanabe | 250/204 |
| 4,614,864 | 9/1986 | Wu | 250/201 AF |
| 4,620,089 | 10/1986 | Schlichting et al. | 250/201 AF |
| 4,633,074 | 12/1986 | Kunz | 250/201 PF |

*Primary Examiner*—David C. Nelms
*Assistant Examiner*—William L. Oen
*Attorney, Agent, or Firm*—Antonelli, Terry & Wands

[57] ABSTRACT

A method of auto-focusing suitable for fine patterns of LSIs and an apparatus therefor, particularly applied for checking the geometry of a circuit pattern of a semiconductor device formed on an LSI wafer. A stripe pattern is projected on a specified location on an object to be checked and contrast of an image of the stripe pattern is used for focusing. The specified location is imaged by an optical system and detected simultaneously by two detectors. A position at which contrast of an output signal of one detector coincides with that of the other detector is determined to be an in-focus position. Am image of a multi-layer pattern representative of the circuit pattern is focused on another detector disposed at the in-focus position and detected for checking. The output signal of the detector is divided by mean brightness of the stripe pattern image so as to be normalized. Since the two detectors produce their output signals simultaneously, the difference between the output signals is normalized to improve accuracies of computation.

12 Claims, 13 Drawing Figures

FIG. 2
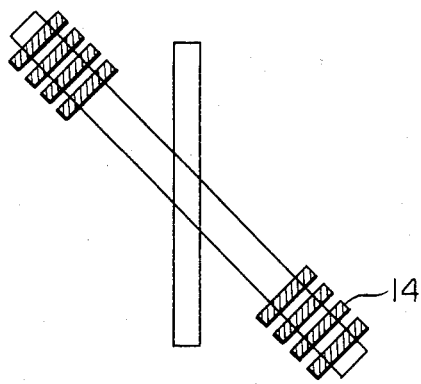
FIG. 3
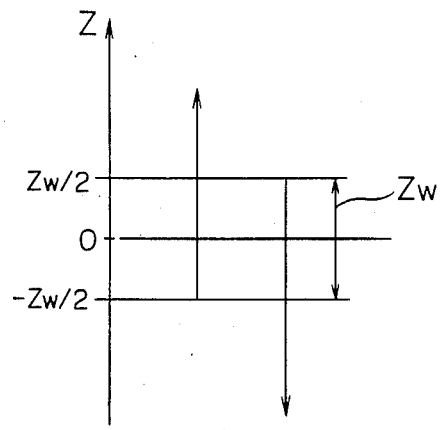
FIG. 4
14 STRIPE PATTERN MEMBER
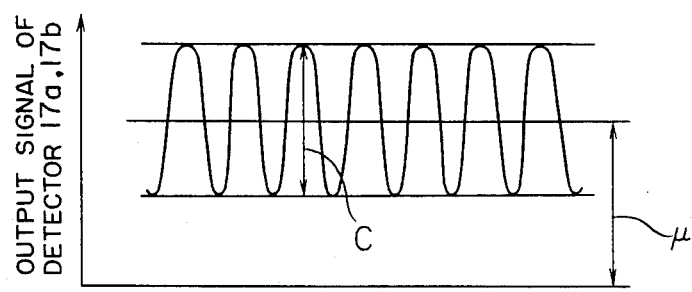

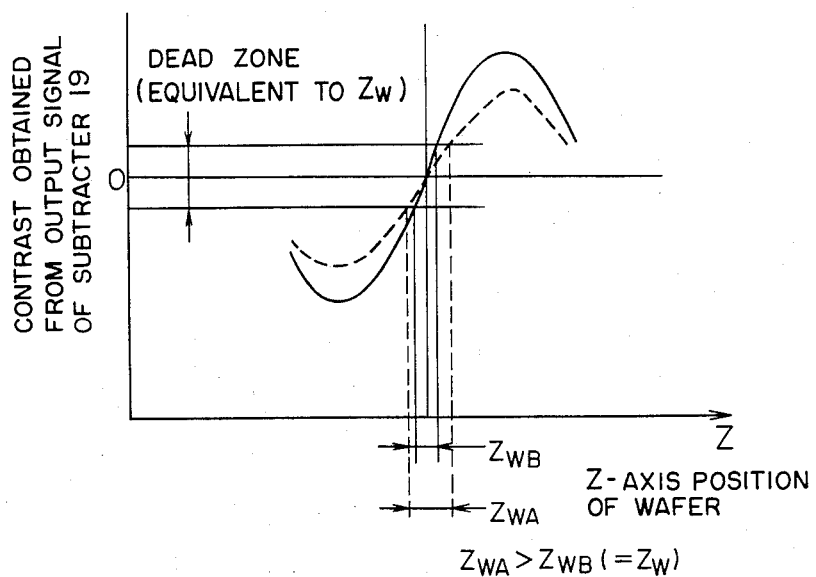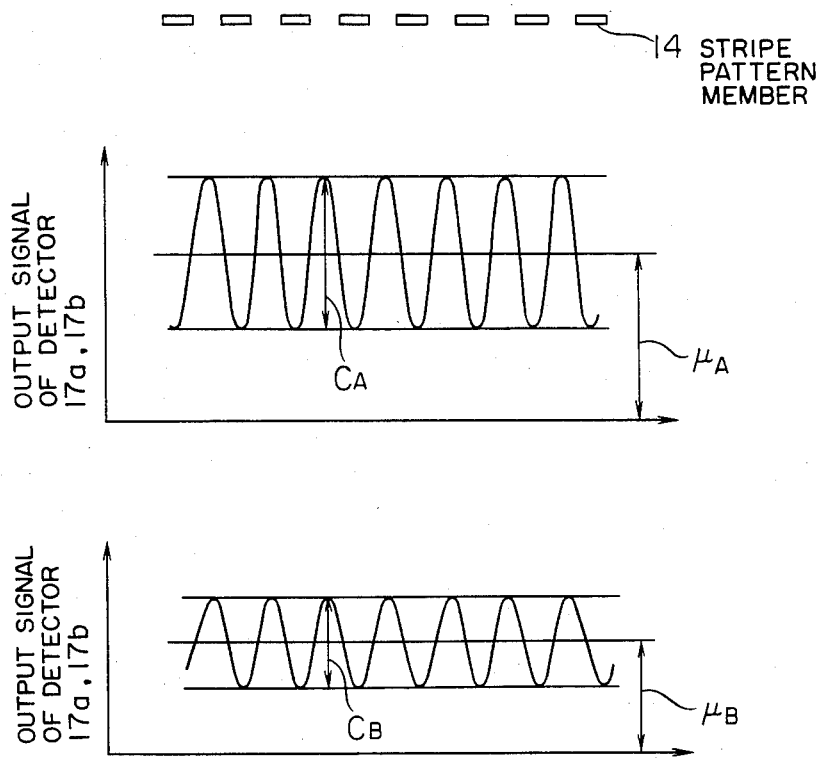

AUTOMATIC FOCUSING METHOD AND APPARATUS UTILIZING CONTRASTS OF PROJECTED PATTERN

BACKGROUND OF THE INVENTION

This invention generally relates to geometry checking arts for checking the geometry of a circuit pattern of a semiconductor device formed on an LSI wafer and more particularly to a method of auto-focusing and an apparatus therefor.

Integrated circuits such as LSIs have a tendency toward high density packaging and miniaturization. In formation of fine patterns for use in such integrated circuits, it often happens that pattern defects occur even if the formation process is very carefully handled, and careful inspection is required. In primitive inspection, a number of inspectors check patterns by the eye using a microscope and their eyes get tired with a long term inspection to overlook many defects, causing problems in quality control. It is therefore desired to automate the production process but in automating the inspection process, there still remains a significant problem of focusing.

Many proposals have been made mainly in techniques of auto-focusing of cameras. For example, Japanese Patent Unexamined Publication No. 58-91409 discloses an arrangement to be described below.

More particularly, a light beam emitted from a light source is irradiated on a circuit pattern formed on a wafer, a resulting image of the circuit pattern is magnified at high magnification and focused on a photoelectric converter by means of an objective lens, and the optical image is converted by the photoelectric converter into an electric signal which is used for judgement of defects. Simultaneously, the optical image of the circuit pattern at the same location is also projected on two photoelectric converters disposed at optically conjugate front and rear planes which are equi-distant from the former photoelectric converter. The output signals of the photoelectric converters are computed at a computing circuit in accordance with a predetermined evaluation function to determine amounts of blur, and under-focus, in-focus and over-focus are decided on the basis of the evaluation values.

This technique seems to be applicable to checking of patterns of LSIs but practically, an object to be checked is inherently different from an object to be photographed and various difficulties are encounted in checking of patterns.

More particularly, an LSI pattern standing for an object to be checked is very fine, generally in the order of 1 $\mu$m, and the pattern is of a multi-layer structure, with the result that the quantities of light incident to the optical system greatly differ one location to another subject to focusing. Further, the image to be inspected must be magnified at high magnification and therefore it is greatly affected by vibrations. Moreover, since depending on ambient temperatures, the object to be checked deforms and accuracies of positioning required for an object carriage vary, it is needed that focusing be carried out continuously.

SUMMARY OF THE INVENTION

An object of this invention is to provide a method of auto-focusing suitable for fine patterns of LSIs and an apparatus therefor.

According to this invention, a stripe pattern is projected on a specified location on an object to be checked and contrast of an image of the stripe pattern is used for focusing. The specified location on which a stripe pattern is projected is imaged by an optical system and detected simultaneously by two detectors. A position (Z-axis) at which contrast of an output signal of one detector coincides with that of the other detector is determined to be an infocus position. An image of a multi-layer pattern is focused on another detector disposed at the in-focus position and detected for checking accuracy of the focusing.

The output signal of the detector is divided by mean brightness of the stripe pattern image so as to be normalized. Since the two detectors produce their output signals simultaneously, the difference between the output signals is normalized to improve accuracies of computation.

In order to recognize the direction of defocusing, the difference between the detector output signals is normalized and thereafter used for focusing.

Amplitude and phase of the detector difference output signal are determined to thereby eliminate influence of offset of the detector in contrast computation.

BRIEF DESCRIPTION OF THE DRAWINGS

FIG. 2 is a plan view showing an example of a stripe pattern member used for the auto-focusing apparatus of FIG. 1;

FIG. 3 is a diagram for explaining a dead zone used for preventing vibration of the wafer;

FIG. 4 shows a waveform of an output signal from an image sensor;

FIG. 7 is a graphical representation for explaining variation in focusing accuracies corresponding to the dead zone;

FIG. 8 shows changes in contrast due to different materials;

DESCRIPTION OF THE PREFERRED EMBODIMENT

A preferred embodiment of the invention will now be described with reference to FIGS. 1 to 11b.

Figure 1:
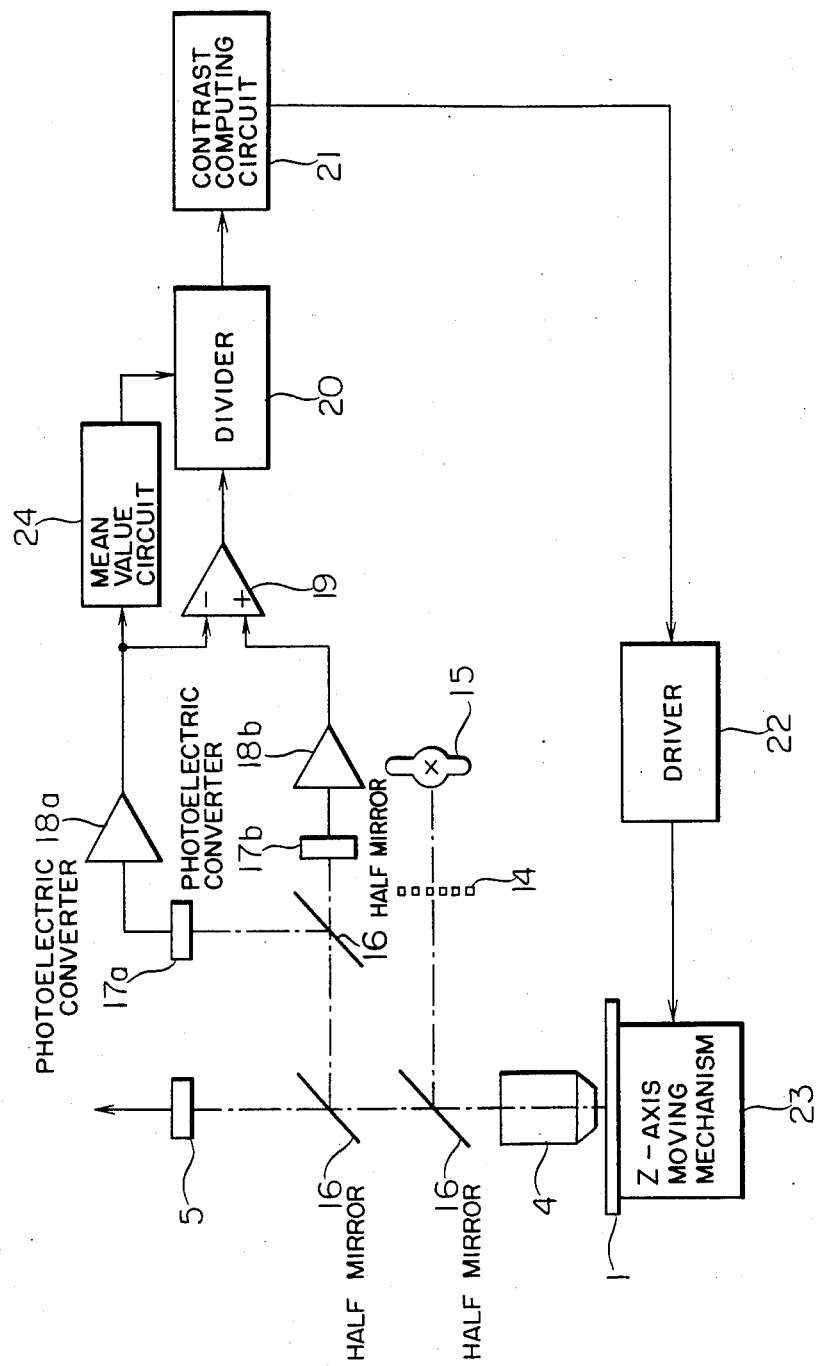
FIG. 1 is a schematic view showing an auto-focusing apparatus according to an embodiment of the invention.

FIG. 1 shows the construction of an auto-focusing apparatus embodying the invention. A circuit pattern formed on a wafer is irradiated with a light beam emitted from a light source 15 such as a mercury-arc lamp, and a resulting optical image of the circuit pattern is magnified at high magnification and focused on a photoelectric converter 5 by means of an objective lens 4. The photoelectric converter 5 converts the optical image into an electric signal which is used for judgement of defects. A planar pattern member 14 having a transparent portion and a light-shielding portion is inserted in an optical path of the irradiation beam and irradiated with the light beam from the light source 15 to project a light-and-shade or stripe pattern upon the wafer 1. Stripe pattern image upon the wafer 1 is distinctly representative of an irradiated portion and a nonirradiated portion and provides a more sharp pattern image than the optical image of the circuit pattern on the wafer. The stripe pattern image superimposed on the circuit pattern image is detected by photoelectric converters 17a and 17b. The photoelectric converters 17a and 17b are disposed at optically front and rear positions which are optically equi-distant from the photoelectric converter 5 for detection of the circuit pattern, that is, at conjugate planes with respect to an expected focal plane of the optical system, and they are operated synchronously.

In an example shown in FIG. 2, linear image sensors are used as the photoelectric converters for detection of the stripe pattern and circuit pattern, and a white and black stripe pattern member is used as planar pattern member 14. To avoid interference with the circuit pattern having orthogonal wiring on an object to be checked, a 45° inclined parallel stripe pattern is projected upon a location which is outside a view field for detection of the circuit pattern, and its image is detected by the stripe pattern detection linear sensors. Particularly, the opposite stripe pattern sections are separated from each other through an intermediate transparent portion so as not to overlap the circuit pattern detection view field. The inclination of the stripe pattern may optionally be determined as far as the stripe pattern is projected upon a location at which it is most unaffected by the circuit pattern.

Returning to FIG. 1, the projected stripe pattern is imaged by the linear image sensors 17a and 17b by way of half mirrors 16. When the wafer is brought into infocus, that is, an image of the circuit pattern is formed at an optically middle position between the linear image sensors 17a and 17b, output electrical signals from the image sensors 17a and 17b coincide with each other. This is because the two linear image sensors 17a and 17b image the same location on the wafer at the same timing so that exactly the same circuit pattern and stripe pattern can be imaged by these image sensors and in addition, even if the light source 15 flickers, such fickering is shared by the two image sensors 17a and 17b.

The output signals of the linear image sensors 17a and 17b are amplified by amplifiers 18a and 18b and subtracted from each other by a subtracter 19. By controlling driver 22 of a mechanism 23 for moving the wafer 1 in the Z-axis direction such that the difference becomes zero, the wafer can be brought into in-focus and the linear image sensor 5 can always detect a clear image. Accordingly, the above construction can completely solve the problems encountered in the prior art.

Practically, however, such a factor as noise inherent to the linear image sensors makes it difficult to bring their output signals into exact coincidence. Consequently, when the Z-axis wafer moving mechanism is so controlled as to bring the output signals of the linear image sensors 17a and 17b into coincidence, it is required for the mechanism 23 to continuously move upwards or downwards even though the wafer being nearly in focus and eventually, this mechanism vibrates. The vibration of the Z-axis wafer moving mechanism can be suppressed by moving it at a very small pitch but focusing speed is decreased and response characteristics are impaired. Thus, in order to improve the response characteristics and solve the adverse vibration of the wafer, a dead zone is introduced as exemplified in FIG. 3. The dead zone has a width Zw extending between an over-focus and an under-focus. When the wafer surface is moved upwards until it becomes defocused by exceeding $Z_w/2$, the Z-axis moving mechanism is so controlled as to move downwards. Conversely, when the wafer surface becomes defocused by exceeding $-Z_w/2$, the Z-axis moving mechanism is moved upwards. In this manner, the vibration of the wafer can be prevented. This width Zw of the dead zone determines accuracy of focusing.

Figure 5A:
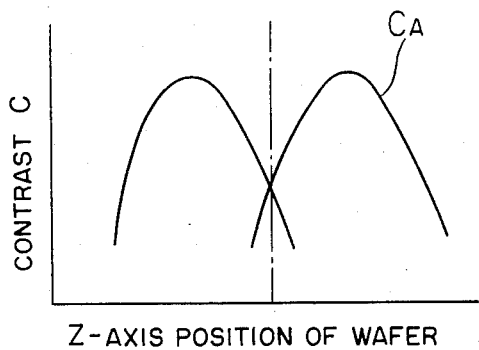
FIGS. 5a and 5b are graphs showing changes in contrast.
Figure 5B:
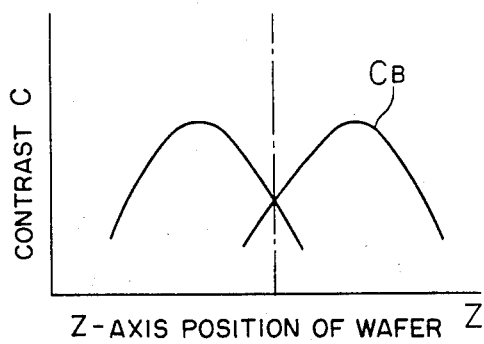
Figure 6:
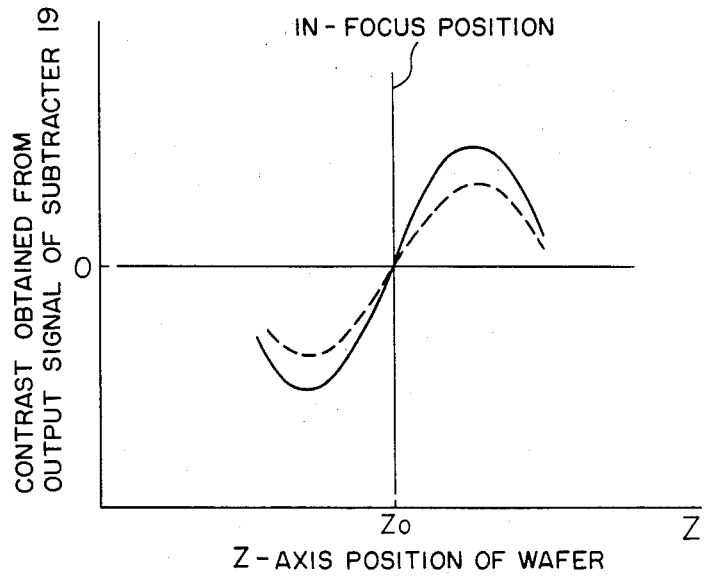
FIG. 6 is a graph for explaining contrast obtained from an output signal of a subtracter.

FIG. 4 exemplifies a waveform of the output signal actually produced from the image sensor 17a or 17b. To eliminate influence of offset of the detector, contrast C corresponding to an illustrated amplitude is set. The contrast C changes, as shown in FIGS. 5a and 5b, with the kind of a wafer to be checked and the projection location on the chip even when the wafer is in focus. The amounts of changes in the contrast are smaller than the amplitude illustrated in FIG. 4. The change in contrast C is due to the fact that intensity of light and shade of the stripe pattern image varies depending on a material of the circuit pattern on the chip upon which the stripe pattern 14 is projected. Accordingly, contrast obtained from an output signal of the subtracter 19 varies with differences in reflection factor, as shown in FIG. 6. Because of variation in the contrast obtained from the output signal of the subtracter 19, the dead zone width Cw in terms of contrast as shown in FIG. 7 which is equivalent to focusing accuracies $\pm Z_w/2$ set in accordance with the contrast obtained from the output signal of the subtracter 19 corresponds to an amount of Z-axis movement $Z_{WB}$ ($=Z_w$) or $Z_{WA}$ of wafer 1 depending on the kind of wafer and the projection location on the chip, thereby causing irregularity in focusing accuracies. Especially, at a location where the circuit pattern is made of a material of low reflection factor, $Z_{WA} >> Z_{WB}$ is held and focusing accuracies are degraded. Therefore, it is necessary to normalize the output signal of the subtracter 19 shown in FIG. 1 in order to ensure highly accurate focusing irrespective of the kind of wafer and the projection location on the chip.

Thus, to maintain uniformity of the focusing accuracies, a normalizing circuit is employed which comprises a mean value circuit 24 and a divider 20 as shown in FIG. 1. Generally, when imaging a material of high reflection factor and a material of low reflection factor, the output signal of the linear image sensor assumes contrast $C_A$ and mean brightness $\mu A$ for the former material which are higher than contrast $C_B$ and mean brightness $\mu B$ for the latter material. This phenomenon is indicated by $$\frac{C_A}{C_B} = \frac{\mu A}{\mu B}.$$

Figure 9:
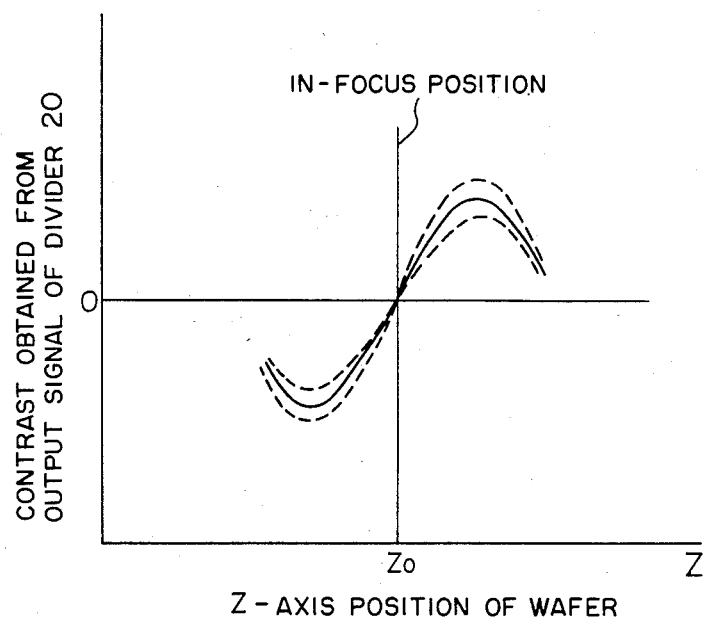
FIG. 9 is a graphical representation for explaining a normalized contrast curve.
Figure 10:
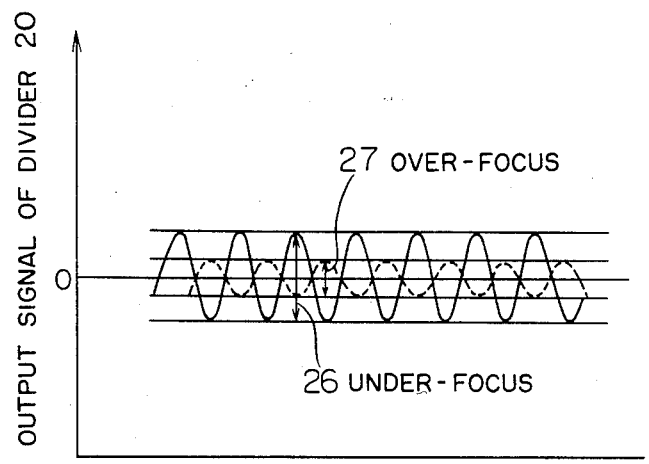
FIG. 10 is a waveform diagram showing output signals of a subtracter.

Accordingly, if the output signal of one of the two linear image sensors is averaged at the mean value circuit 24 to obtain mean brightness, $\mu$, and the output signal of the subtracter 19 is divided at the divider 20 by the mean brightness $\mu$ so as to be normalized, then a contrast curve as shown in FIG. 9 will be obtained which is not affected by the difference in reflection factor, thereby ensuring that highly accurate auto-focusing can be attained which is not affected by the kind and material of wafer. Practically, as shown in FIG. 1, only one process is employed for calculation of contrast at the final stage. Specifically, a contrast computing circuit 21 computes amplitude and phase of an output signal of the divider 20 based on which the Z-axis wafer moving mechanism is controlled. FIG. 10 exemplifies different output signals of the divider 20. From these output signals, the contrast computing circuit 21 computes amounts of contrast 26 and 27 and makes a decision as to focusing on the basis of magnitude and phase of each contrast 26 or 27.

The auto-focusing apparatus described so far is particularly adapted for checking a multi-layer pattern made of different kinds of materials. The arrangement of FIG. 1 is established especially for improving focusing accuracies with a view to eliminating influence of materials of the wafer to be checked, influence of pattern density and introduction of errors into contrast computation and can attain highly accurate focusing without impairment of the response characteristics.

Further, by storing the contrast curve shown in FIG. 9 which is obtained from the normalization, it is possible to decide an in-focus state and to know a displacement from an in-focus position Zo. Consequently, the focusing can be attained at very high speeds by vertically moving the wafer in accordance with the displacement by means of the Z-axis moving mechanism.

Figure 11A:
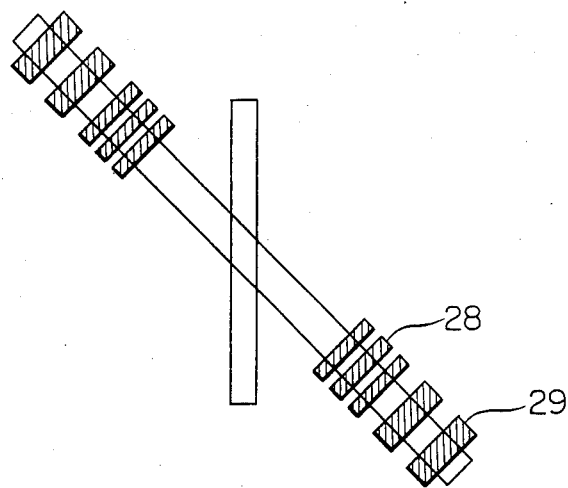
FIG. 11a is a plan view showing another example of the stripe pattern member used for the auto-focusing apparatus of FIG. 1.
Figure 11B:
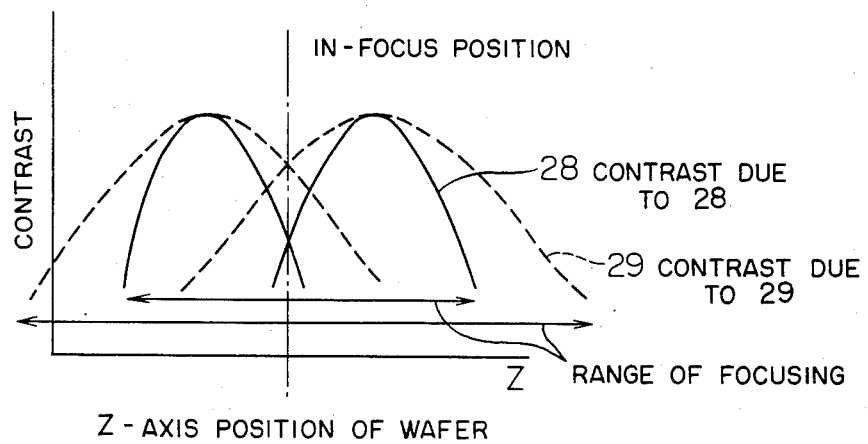
FIG. 11b is a graphical representation for explaining contrast when the stripe pattern member of FIG. 11a is used.

FIG. 11a shows another example of the stripe pattern. In this example, stripes of two different widths, spaced apart at two different intervals, are used in combination. A projected pattern 28 corresponding to a stripe pattern section of narrow spacing tends to blur i.e., has small contrast, upon occurrence of a slight amount of defocusing and therefore it is effective for focusing with high accuracies but has a narrow range of focusing. On the other hand, a projected pattern 29 corresponding to a stripe pattern section of wide spacing tends to hardly blur, i.e., has high contrast, even upon occurrence of defocusing, giving rise to degraded focusing accuracies but a wide range of focusing. Taking advantage of the two sections of stripe pattern, as shown in FIG. 11b contrast obtained from the projected pattern 29 is used when the displacement from the in-focus position Zo is large while contrast obtained from the projected pattern 28 is used when the displacement from the in-focus position Zo is small, thereby broadening the range of focusing without degrading focusing accuracies.

As has been described, the present invention permits highly accurate pattern detection irrespective of the kind of wafer and the projected location on the chip and especially, permits highly accurate auto-focusing for the wafer made of different materials of different reflection factors.

According to the invention, therefore, a multilayer pattern on an LSI wafer can be detected with high accuracies and checking of its geometry can be automated.

We claim:

1. A method of auto-focusing comprising the steps of:
    projecting a planar pattern member having at least a transparent portion and a light-shielding portion on an object so as to form a pattern of at least a light and dark portion;
    forming an image of a projected pattern by an optical system;
    detecting said image of the projected pattern by two photoelectric converters disposed at optically conjugate front and rear planes with respect to an expected focal plane of said optical system and providing output signals from said two photoelectric converters indicative of contrast of the detected image of the projected pattern having at least a light and dark portion; and
    moving said object so as to obtain a difference of zero between the output signals of said two photoelectric converters, thereby obtaining an in-focus state at said expected focal plane.

2. An auto-focusing method according to claim 1 wherein said planar pattern member comprises a stripe pattern having stripes of two or more different widths which are spaced apart at two or more different intervals.

3. An auto-focusing method according to claim 1 wherein a dead zone insensitive to the difference between the output signals of said two photoelectric converters is provided for preventing said object from vibrating.

4. An auto-focusing method according to claim 1 wherein the difference between the output signals of said two photoelectric converters is divided by one of said output signals so as to be normalized.

5. An auto-focusing method according to claim 1 wherein said planar pattern member has a stripe pattern of periodically arranged stripes, amplitude and phase of the difference between the output signals of said two photoelectric converters are determined, and a focusing state is judged on the basis of the amplitude and phase to obtain the in-focus state.

6. An auto-focusing method according to claim 5 wherein the difference between the output signals of said two photoelectric converters is divided by one of said output signals so as to be normalized, the relation between amplitude and phase of said normalized difference and defocusing is memorized, and a displacement from an in-focus position is computed by referring to stored data.

7. An apparatus for auto-focusing comprising:
    means for projecting a planar pattern member having at least a transparent portion and a light-shielding portion on an object so as to form a pattern having at least a light and dark portion;
    an optical system for forming an image of a projected pattern;
    two photoelectric converters, disposed at optically conjugate front and rear planes with respect to an expected focal plane of said optical system, for detecting said image of the projected pattern and for providing output signals indicative of contrast of the detected image of the projected pattern having at least a light and dark portion; and
    means for moving said object so as to obtain a difference of zero between the output signals of said two photoelectric converters, thereby obtaining an in-focus state at said expected focal plane.

8. An auto-focusing apparatus according to claim 7 wherein said planar pattern member comprises a stripe pattern having stripes of two or more different widths which are spaced apart at two or more different intervals.

9. An auto-focusing apparatus according to claim 7 further comprising means for providing a dead zone insensitive to the difference between the output signals of said two photoelectric converters so as to prevent said object from vibrating.

10. An auto-focusing apparatus according to claim 7 further comprising means for dividing the difference between the output signals of said two photoelectric converters by one of said output signals so that said difference is normalized.

11. An auto-focusing apparatus according to claim 7 wherein said planar pattern member has a stripe pattern of periodically arranged stripes, said apparatus further comprising means for determining amplitude and phase of the difference between the output signals of said two photoelectric converters so that a focusing state is judged on the basis of the amplitude and phase to obtain the in-focus state.

12. An auto-focusing apparatus according to claim 11 further comprising means for dividing the difference between the output signals of said two photoelectric converters by one of said output signals so that said difference is normalized, means for storing the relation between amplitude and phase of said normalized difference and defocusing, and means for computing a displacement from an in-focus position by referring to the stored amplitude and phase.

* * * * *